United States Patent [19]

Peyman

[11] Patent Number: 4,470,159

[45] Date of Patent: Sep. 11, 1984

[54] KERATOPROSTHESIS

[76] Inventor: Gholam A. Peyman, 535 N. Michigan #3001, Chicago, Ill. 60611

[21] Appl. No.: 354,474

[22] Filed: Mar. 3, 1982

[51] Int. Cl.³ .............................. A61F 1/16; A61F 1/24
[52] U.S. Cl. ......................................................... 3/13
[58] Field of Search ........................................ 3/13, 1

[56] References Cited

U.S. PATENT DOCUMENTS

| 3,458,870 | 8/1969 | Stone | 3/13 |
| 3,945,054 | 3/1976 | Fedorov et al. | 3/13 |
| 4,074,368 | 2/1978 | Levy, Jr. et al. | 3/13 |
| 4,315,337 | 2/1982 | Choyce | 3/13 |

FOREIGN PATENT DOCUMENTS

| 2727410 | 12/1978 | Fed. Rep. of Germany | 3/13 |
| 2071352 | 9/1981 | United Kingdom | 3/13 |

OTHER PUBLICATIONS

"Present Status of Prosthokeratoplasty" by R. Castroviejo et al., America Journal of Ophthalmology, Oct. 1969, vol. 68, No. 4, pp. 613–625.

Primary Examiner—Ronald L. Frinks
Attorney, Agent, or Firm—Thomas A. Kmiotek

[57] ABSTRACT

A keratoprosthesis having a generally cylindrical lens structure, extending anteriorly to the corneal stroma and posteriorly through the pupil and into the posterior chamber, and an anterior chamber supporting means. Certain preferred embodiments of the invention further include an anteriorly removable lens element, a lens structure having a posterior end of predetermined curvature for functioning as an intraocular permanent lens and an intracorneal flange support. The keratoprosthesis is virtually incapable of being extruded and permits subsequent visual correction without further surgical intrusion into the anterior chamber.

28 Claims, 13 Drawing Figures

U.S. Patent  Sep. 11, 1984  Sheet 1 of 2  4,470,159
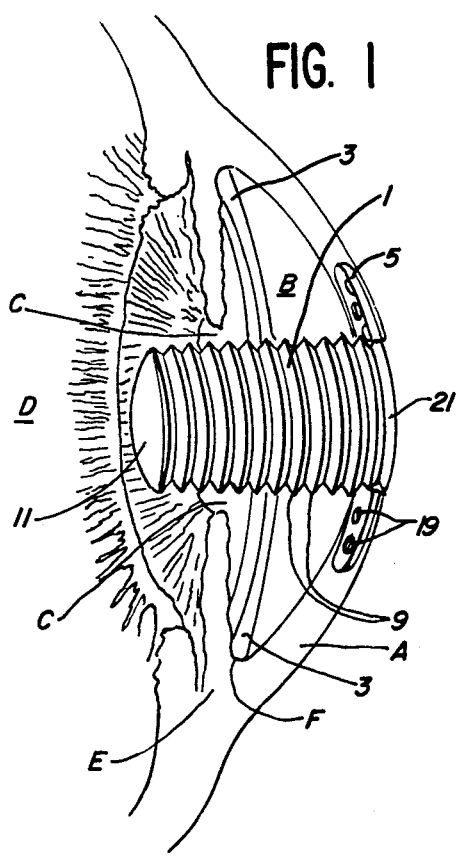
FIG. 1
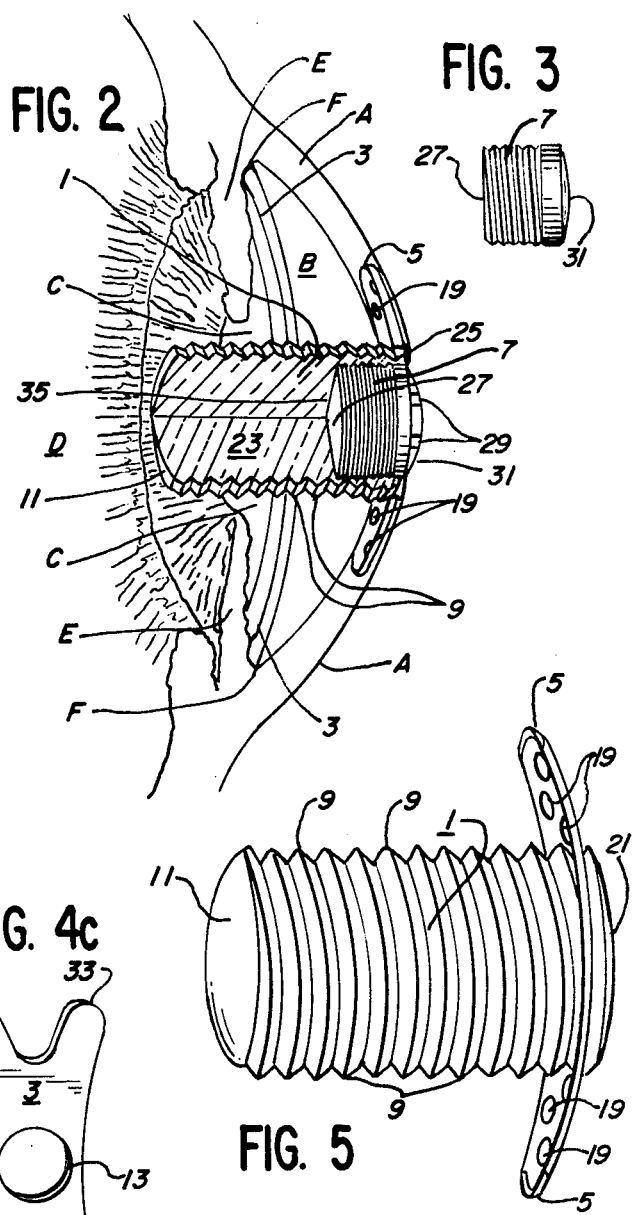
FIG. 2    FIG. 3

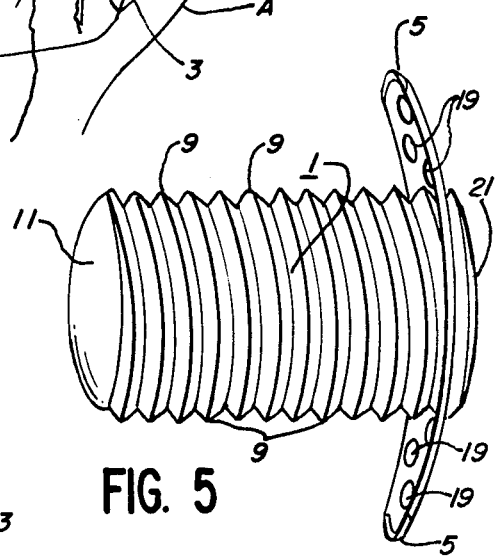
FIG. 5
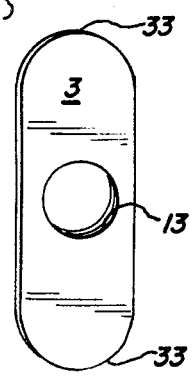 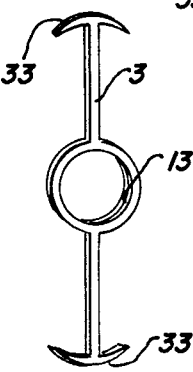
FIG. 4d  FIG. 4e
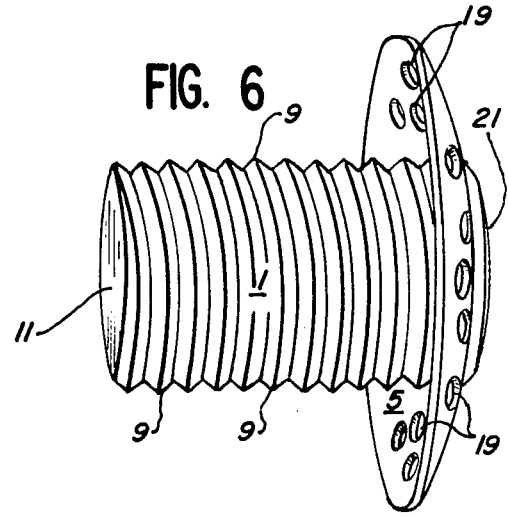
FIG. 6

KERATOPROSTHESIS

FIELD OF THE INVENTION

This invention generally relates to ophthalmic prosthetic devices. It particularly relates to a keratoprosthesis for replacing a part of the cornea in a mammalian eye which has suffered severe corneal damage but which still has good light perception and projection.

BACKGROUND OF THE INVENTION

Blindness due to corneal causes has long been a challenge to ophthalmic surgeons treating the anterior segment of the eye. In many cases, the blindness-causing injury has altered the optical clarity and refractive abilities of the cornea to such an extent that the body cannot satisfactorily repair it, but has left the eye's light perception and projection relatively intact. In such cases, the only alternatives for improving vision are a corneal transplant (keratoplasty) or a prosthesis. Corneas exhibiting severe scarring or vascularization resulting from chemical burns are often irreparable through keratoplasty, whether or not anterior segment reconstruction is performed. Indeed, in these instances and where there is a history of repeated keratoplasty failure because of the inability of the recipient's body to tolerate or provide adequate nutrition to the graft, or where there is the presence of keratitis sicca or pemphigoid, use of a keratoprosthesis is the only alternative for improving vision in the eye.

Investigators in this field have been working for more than a century on the development of simple lens keratoprostheses for replacing and functioning as part of the cornea. See, Cardona, "Keratoprosthesis", *American Journal of Ophthalmology*, Vol. 54, 284–294 (1962). Typically, these keratoprostheses are implanted in the corneal stroma or sutured to it; hence, the only supporting structure for the keratoprosthesis is the cornea itself. Any intraocular portion of the prosthesis is thus left to hang, unsupported, in the anterior chamber.

Complications encountered with presently used keratoprostheses include extrusion of the implant following a progressive erosion or aseptic necrosis of the corneal tissue surrounding the implant. This, in part, may be caused by the stresses placed on the surrounding tissue by the movement of an unsupported implant. Another complication encountered is the tendency for corneal membrane tissue to overgrow the intraocular portion of the prosthesis, thereby interfering with light perception and altering light projection. This tissue overgrowth can, as well, lead to implant extrusion. Additional problems encountered in the use of keratoprostheses presently used are irritation and ulceration of the surrounding tissues which, too, eventually lead to extrusion of the implant. Even in some of the most impressive clinical studies involving keratoprostheses, these complications have resulted in extrusion failure rates generally over 10%. See, Cardona, "Mushroom Transcorneal Keratoprosthesis", *American Journal of Ophthalmology*, Vol. 68, No. 4, 604–612 (October 1969) and Castroviejo, et al., "Present Status of Prosthokeratoplasty", *American Journal of Ophthalmology*, Vol. 68, No. 4, 613–625 (October 1969).

Another limitation of presently used keratoprostheses is the fact that the only optically functional lens portion of the prosthesis is permanently fixed in the anterior chamber. Once the keratoprosthesis is implanted, therefore, minor refractive errors of the eye must be corrected by eyeglasses. There exist no available keratoprostheses in which adjustments of the optical characteristics of the lens portion may be accomplished after implantation without invasive surgical techniques. Furthermore, none exist which would permit an entirely new optical lens to be utilized without such procedures. Any surgical intrusion for this purpose carries with it the risks accompanying the loss of intraocular pressure and is to be avoided where possible.

SUMMARY OF THE INVENTION

The present invention overcomes the drawbacks of the prior art by providing a keratoprosthesis which, when implanted, becomes an integral part of the eye, is adequately supported therein and is virtually impossible to extrude.

In its simplest form, the keratoprosthesis of the invention comprises a generally cylindrical lens structure, preferably of solid construction, and an anterior chamber supporting means. The lens structure is of sufficient length to extend anteriorly into the corneal stroma and posteriorly through the pupil and into the posterior chamber. Because the lens structure extends into the posterior chamber, corneal membrane tissue growth occurring subsequent to the implant procedure cannot interfere with the transmission of light through its posterior end.

The lens structure is supported at two separate places; anteriorly by attachment to the corneal stroma and posteriorly by the anterior chamber supporting means, which is anchored by the contact of its outer edges with the anterior chamber angle. Preferably, the anterior chamber supporting means is substantially planar and is of such dimensions and of such shape as to permit it to be torsionally anchored in the anterior chamber by means of contact of its outer edges with the anterior chamber angle.

A preferred embodiment of the invention includes a lens structure having an anteriorly removable lens element which can be either replaced or exchanged for another element of differing dioptic power without surgical intrusion into the anterior chamber. Preferably, in such an embodiment, the cylindrical lens structure has an axially disposed internally threaded receptacle for receiving the removable lens portion, which itself has a threaded external surface. Thus, the lens portion is readily screwed in or out of the receptacle without the necessity of altering or exchanging the cylindrical lens structure itself by surgical means. To facilitate the removal and replacement of such a threaded lens element, one or more channels, ridges or other variations from the smooth rounded anterior surface of the lens element are preferably provided for accommodating a tool adapted to engage these surface articulations.

In order to prevent refraction or scattering of light as it passes through the removable lens element and into the solid lens structure, it is important that the shape of the posterior end surface of the removable lens element be complementary to that of the posterior end surface of the cylindrical receptacle so as to eliminate any gap between those surfaces. Preferably, both surfaces are flat and are perpendicular to the longitudinal axis of the lens structure.

A further preferred embodiment of the invention includes a generally cylindrical lens structure having a posterior end of predetermined curvature so that it acts as an additional lens. The posterior end of the lens structure is shaped in the desired fashion prior to implantation in order to provide a permanent intraocular lens of a specified dioptic power. Subsequent changes in the eye which require adjustment of the optical characteristics of the keratoprosthesis may then be made by changing the removable lens element of the lens structure without the necessity of surgically disturbing the intraocular portion of the lens structure.

The lens structure, including the removable lens element, may be constructed of any suitable approved transparent material, including those commonly used for the construction of keratoprostheses or contact lenses, but is preferably constructed from one of the following materials: glass, a methyl acrylate plastic, such as that sold under the trademark PLEXIGLAS®, or silicone.

As a means for further supporting and securing the keratoprosthesis of the invention, an intracorneal support may be provided which preferably conforms to the shape of the cornea. The intracorneal supporting means can be secured to the outer surface of the anterior end of the lens structure by being press-fit thereto, or it can be constructed as an integral part of the lens structure. Preferably, however, the outer surface of the anterior end of the lens structure is threaded and the intracorneal support has a central threaded aperture so that the latter may be screwed onto the former. In order to provide a matrix for encouraging the growth of corneal stroma tissue which will secure the intracorneal support and to provide for ease of suturing, the intracorneal support is preferably constructed of an apertured or perforated material. Further encouragement of corneal stroma tissue growth may result from providing an intracorneal supporting means constructed, at least in part, from bone or of a knitted fibrous material, such as the synthetic polyester fiber sold under the trademark DACRON®. While the shape of the intracorneal supporting means may be selected to meet the particular requirements of the individual patient, a substantially circular or oblong member is preferred.

As previously discussed, the anterior chamber supporting means is preferably substantially planar, is anchored at its outer edges by contact with the anterior chamber angle and expands the anterior chamber to a limited degree. In the most preferred embodiment, the anterior chamber supporting means is of such planar dimensions and of such shape as to permit it to be torsionally anchored in the anterior chamber by means of contact with the anterior chamber angle. The anterior chamber supporting means may be constructed in whole or in part of bone, metal, ceramic or virtually any other material found suitable, but it is preferably constructed of a methyl acrylate plastic, such as that sold under the trademark PLEXIGLAS®, or silicone, and it may be formed in a variety of shapes.

The anterior chamber supporting means is provided with a central aperture through which the posterior portion of the cylindrical lens structure is inserted. Preferably, at least a portion of the outer surface of the lens structure and the inner surface of the anterior chamber supporting means are threaded so that, after the insertion, placement and anchoring of the anterior chamber supporting means, the lens structure may be screwed into position through the threaded aperture and thereby attached to and supported by the anterior chamber supporting means.

Another preferred means of supporting the lens structure is to provide an anterior chamber supporting means of double cross-member construction which is of a thickness less than the distance between the thread ridges on the outer surface of the lens structure. In this embodiment, the cross-members of the supporting means are so spaced as to be capable of riding in the thread grooves of the lens structure so as to provide the necessary attachment and support.

Thus, in the preferred embodiments of the invention, the combination of the intracorneal supporting and the anterior chamber supporting means acts to secure and support the lens structure, rendering it substantially immobile and substantially immune to extrusion.

The surgical procedure by which a prefered embodiment of the keratoprosthesis of the invention is implanted in the eye is substantially as follows:

The corneal limbus is first delineated, and then an arc-shaped incision is made at the superior limbus. This incision preferably defines an arc of between about 100 degrees and about 180 degrees. The lens is then removed, and the anterior chamber supporting means is implanted in the anterior chamber. A needle is then introduced through the incision and is inserted into the center of the cornea from the posterior side in order to define the location of that center. The exit point of the needle is then marked, the needle is removed and the corneal incision is closed. Closure of the incision may be by running or interrupted sutures.

Using the needle mark as a guide, a corneal trephine is positioned around the central portion of the cornea. A corneal button is then dissected and excised, following which a circular, vertical incision is made in the cornea to reach a depth of half the corneal thickness. The cornea is next dissected in a circular fashion around the corneal opening to the extent necessary to accommodate the intracorneal supporting means.

The lens structure is then inserted through the corneal opening, directed to the center of the anterior chamber supporting means, and threaded into the supporting means until the anterior end of the lens structure is at the level of the cornea. The intracorneal supporting means is then threaded onto the lens structure until it, too, is at the level of the cornea. Next, the anteriorly removable lens element is screwed into the lens structure. Finally, the previously dissected circular corneal segment is sutured over the intracorneal supporting means.

In order to accelerate the healing process, the conjunctiva may be brought down to cover both the corneal incision and the anteriorly removable lens element and left in that position for a period of a few weeks. Subsequently, the lens element is exposed by excising the overlying portion of the conjunctiva.

Once the lens element is exposed, the refractive power of the patient's eye is measured. A lens element can then be chosen which will give the patient the refractive power of an emmetropic eye.

As an alternative implant procedure, the first incision may be made so as to completely penetrate the cornea so that both the lens structure and the anterior chamber supporting means can be implanted at the same time. Corneal tissue is then excised to accommodate the anterior portion of the lens element. The remainder of the procedure is as described above.

Accordingly, it is an object of the invention as hereinabove described to provide a new keratoprosthesis which is permanently incorporated into the eye and which becomes an integral part thereof.

A further object is to provide a new multi-element keratoprosthesis having means for supporting and retaining the implant within the eye so as to render its extrusion virtually impossible and to avoid requiring the cornea to bear the entire stress of supporting the intraocular portion of the prosthesis.

A related object is to provide a keratoprosthesis having sufficient support to prevent it from moving about within the anterior chamber, thereby causing irritation and ulceration of the surrounding tissue.

A still further object of the invention is to provide a keratoprosthesis having a lens structure which cannot be obstructed by overgrown corneal membrane tissue and which therefore retains its optical properties during and after the healing of the supporting tissue.

An additional object of the invention is to provide a keratoprosthesis having a permanent intraocular lens.

Finally, it is an object to provide a keratoprosthesis having an externally removable lens portion which is replaceable without opening the anterior chamber, thereby avoiding loss of intraocular pressure and the accompanying risk of intraocular infection, and which eliminates the need for corrective eyeglasses as a supplement to the visual correction provided by the prosthesis itself.

Other objects and advantages will be apparent to those skilled in the art from the above discussion, from the following detailed description, from the drawings, and from the claims appended hereto.

BRIEF DESCRIPTION OF THE DRAWINGS

FIG. 1 is an enlarged perspective view of the keratoprosthesis of the invention wherein the related structures of the eye are shown in a partial sectional view.

FIG. 2 is an enlarged perspective sectional view of the keratoprosthesis of the invention wherein the related structures of the eye are shown in a partial sectional view.

FIG. 3 is an enlarged side view of the removable lens portion of the keratoprosthesis of the invention.

FIGS. 4a through 4e are enlarged perspective views of alternative preferred embodiments of the anterior chamber supporting means of the invention.

FIG. 5 is an enlarged perspective view of the combination of an embodiment of the cylindrical lens structure having a curved posterior end for functioning as an intraocular lens and an oblong embodiment of the intracorneal support.

FIG. 6 is an enlarged perspective view of the combination of an embodiment of the cylindrical lens structure having a flat posterior end and a circular embodiment of the intracorneal support.

DETAILED DESCRIPTION

FIG. 1 illustrates the relationship of one preferred embodiment of the invention with respect to the surrounding structures of the eye. As shown therein, the cylindrical lens structure 1 extends anteriorly to the corneal stroma A and posteriorly through the anterior chamber B, through the pupil C and into the posterior chamber D. Details of the iris E, which surrounds the posterior portion of the lens structure 1, are also shown. The posterior end 11 of lens structure 1 has a curved shape so as to permit posterior end 11 to function as an intraocular lens.

Figure 4A:
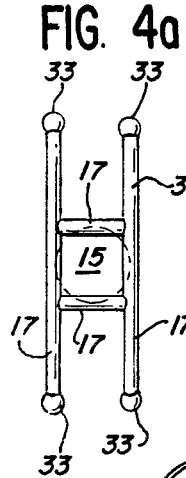
Figure 4B:
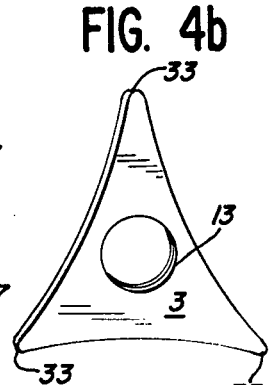
Figure 4C:
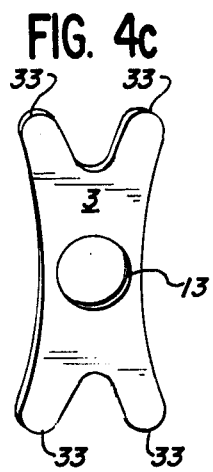

As further shown in FIG. 1, lens structure 1 is supported by anterior chamber supporting means 3 which is firmly anchored in the anterior chamber angle F. Lens structure has threads 9 on its outer surface and it is supported by and attached to anterior chamber supporting means 3 by being screwed into a threaded aperture 13 in supporting means 3 in the embodiments shown in FIGS. 4b, 4c, 4d, 4e and 7 or by being screwed into an aperture 15 formed by substantially parallel cross-members 17 of an embodiment of a supporting means 3 such as shown in FIG. 4a, which embodiment is of a thickness not exceeding the distance between threads 9 of lens structure 1.

Also illustrated in FIG. 1 is intracorneal supporting means 5 which is attached to the outer surface of lens structure 1 and is entirely embedded in the corneal stroma A. Apertures 19 are formed in intracorneal support 5 for encouraging corneal tissue growth through said apertures 19, which growth will both aid the healing process after surgical implantation and anchor the anterior end 21 of the prosthesis more firmly in the eye.

Another preferred embodiment is illustrated in FIG. 2, wherein lens structure 1 is shown in a partial sectional view so as to reveal a threaded removable lens portion or lens element 7, which is shown separately in FIG. 3. In this embodiment, lens structure 1 has a solid posterior portion 23 and an anterior internally threaded receptacle 25 for receiving threaded removable lens element 7. Preferably, both the posterior end of lens element 7 and the posterior surface 29 of receptacle 25 are substantially flat so as to fit face-to-face with no gap between them, thus permitting light to pass through lens element 7 and into the solid portion 23 of lens structure 1 without significant refraction or scattering. It is further preferred, as shown in FIGS. 2 and 3, that the anterior surface 31 of removable lens element 7 be provided with channels 29 or other surface variations for facilitating the removal and insertion of lens element 7 into lens structure 1.

In FIGS. 4a, 4b, 4c, 4d and 4e are illustrated various alternative embodiments of anterior chamber supporting means 3, the function of which has previously been described. In each embodiment, supporting means 3 preferably has two or more rounded points 33 on its perimeter for firmly contacting the anterior chamber angle F of the eye (see FIGS. 1 and 2).

FIG. 5 illustrates one alternative embodiment of the combination of cylindrical lens structure 1 and intracorneal supporting means 5. As shown therein, lens structure 1 is provided with exterior threads 9 for engaging the aperture 13 or 15 of supporting means 3 (see FIGS. 4a–4e) and with curved posterior end 11 for enabling said end 11 to function as an intraocular lens. Intracorneal supporting means 5, attached to the outer surface of lens structure 1 at anterior end 21, is of a modified oblong configuration (see also FIG. 7) and is provided with a multiplicity of apertures 19 for effecting firm intracorneal support by encouraging tissue growth through said apertures.

An alternative embodiment of the above combination is shown in FIG. 6. In this embodiment the posterior end 11 of lens structure 1 is essentially flat and contributes nothing to the dioptic power of the prosthesis. The intracorneal support 5, provided with multiple apertures 19, is essentially circular in shape.

Figure 7:
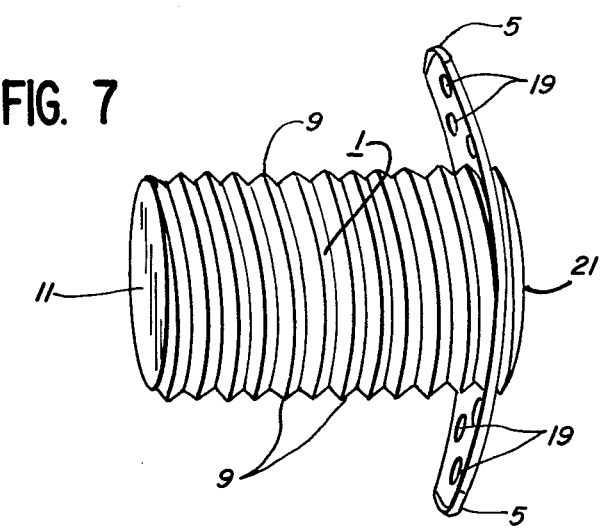
FIG. 7 is an enlarged perspective view of the combination of an embodiment of a lens structure having a flat posterior end and an oblong embodiment of the intracorneal support.

Another embodiment of the above-described combination appears in FIG. 7, wherein an oblong intracorneal support 5 is utilized with a lens structure 1 having a flat posterior end surface 11.

Figure 8:
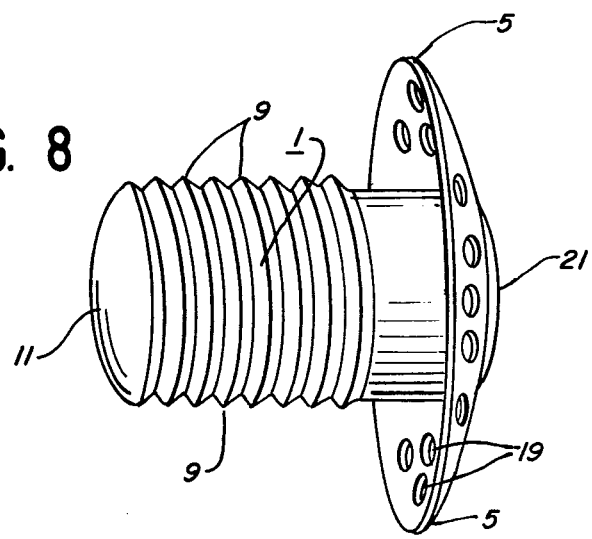
FIG. 8 is an enlarged perspective view of an embodiment of a lens structure, having an outer surface which is threaded only over the portion which will engage the threaded aperture of the anterior chamber supporting means and having a curved posterior end for functioning as an intraocular lens, in combination with a circular embodiment of the intracorneal support.

FIG. 8 illustrates still another alternative embodiment of the combination, wherein the outer surface of the anterior portion of the lens structure 1 is not threaded, but is secured to the circular intracorneal support 5 by being press-fit thereto. In this embodiment, the posterior end 11 of lens structure 1 is curved to provide a permanent intraocular lens.

Figure 9:
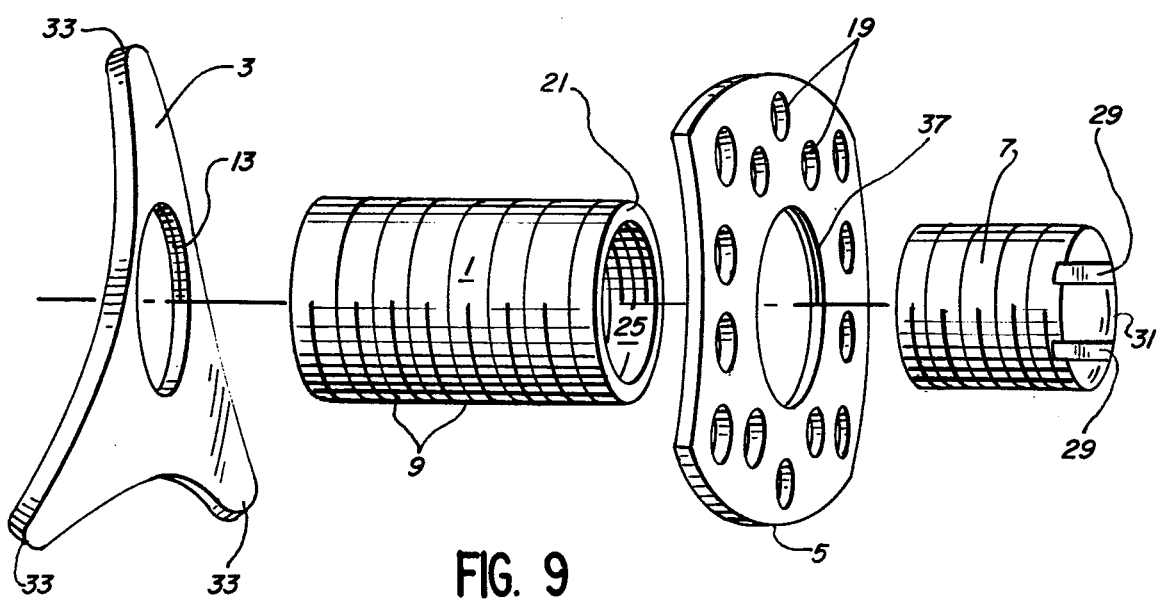
FIG. 9 is an enlarged exploded view of a preferred embodiment of the invention.

FIG. 9, an enlarged exploded view of the keratoprosthesis of the invention, illustrates the assembly of one preferred embodiment thereof. As shown in that view, removable threaded lens element 7 is provided with channels 29 in its anterior surface 31 for facilitating its insertion into internally threaded receptacle 25 of lens structure 1. The length of lens structure 1 is sufficient to extend anteriorly to the corneal stroma and posteriorly through the pupil and into the posterior chamber. Lens structure 1 is provided with exterior threads 9 for engaging threaded aperture 13 of anterior chamber supporting means 3. Supporting means 3 is provided with rounded points 33 on its perimeter for engaging the anterior chamber angle. Intracorneal supporting means 5 is attached to the outer surface of anterior end 21 of lens structure 1 by means of threaded aperture 37 and is provided with a multiplicity of apertures 19 for facilitating its implantation in the corneal stroma.

While the invention has been described herein in detail with reference to alternative preferred embodiments, it is understood that variations, modifications and substitutions of equivalent structural elements may be made without departing from the scope and spirit of this invention.

What is claimed is:

1. A keratoprosthesis comprising a generally cylindrical lens structure, of sufficient length to extend anteriorly into the corneal stroma and posteriorly through the pupil into the posterior chamber wherein said lens structure includes an anteriorly removable lens portion and means for attaching said removable lens portion to said lens structure, and an anterior chamber supporting means.

2. A keratoprosthesis according to claim 1 constructed of a material selected from the group consisting of glass, a methyl acrylate plastic, and silicone.

3. A keratoprosthesis according to claim 1 having an externally threaded, cylindrical, removable lens portion and wherein said attaching means of said lens structure includes a cylindrical threaded receptacle for receiving said externally threaded removable lens portion.

4. A keratoprosthesis according to claim 3 wherein said threaded removable lens portion has an anterior surface having means for facilitating the removal and replacement of said threaded lens portion.

5. A keratoprosthesis according to claim 3 wherein said cylindrical receptacle of said lens structure has a posterior end surface and said removable lens portion has a complementary posterior end surface for effecting substantially coextensive contact with said posterior end surface of said receptacle, whereby light is transmitted from said lens portion to said lens structure without substantial refraction.

6. A keratoprosthesis according to claim 5 wherein said posterior end surface of said receptacle and said posterior end surface of said lens portion are substantially flat.

7. A keratoprosthesis according to claim 1 wherein said lens structure includes a posterior end of predetermined curvature for functioning as an intraocular permanent lens.

8. A keratoprosthesis according to claim 1 further comprising intracorneal supporting means.

9. A keratoprosthesis according to claim 8 wherein said intracorneal supporting means conforms substantially to the shape of the cornea.

10. A keratoprosthesis according to claim 8 wherein said intracorneal supporting means has apertures formed therein.

11. A keratoprosthesis according to claim 8 wherein said intracorneal supporting means includes a portion comprising a knitted fibrous material.

12. A keratoprosthesis according to claim 11 wherein said fibrous material is a polyester synthetic fiber.

13. A keratoprosthesis according to claim 9 wherein said intracorneal supporting means is substantially circular in shape.

14. A keratoprosthesis according to claim 8 wherein said intacorneal supporting means is substantially oblong in shape.

15. A keratoprosthesis according to claim 1 wherein said anterior chamber supporting means is substantially flat and is of such planar dimensions and of such shape as to effect the anchoring of said anterior chamber supporting means through contact with the anterior chamber angle.

16. A keratoprosthesis according to claim 15 wherein said anterior chamber supporting means is of such planar dimensions and of such shape as to effect the torsional anchoring of said anterior chamber supporting means in the anterior chamber.

17. A keratoprosthesis according to claim 15 wherein said substantially flat anterior chamber supporting means is constructed from a material selected from the group consisting of a methyl acrylate plastic and silicone.

18. A keratoprosthesis according to claim 15 wherein said cylindrical lens structure has a threaded outer surface over at least a portion of its length and wherein said anterior chamber supporting means includes means for attachingly receiving the threads on the outer surface of said lens structure.

19. A keratoprosthesis according to claim 18 wherein said attaching means of said anterior chamber supporting means comprises threads formed on the interior surface of an aperture in said anterior chamber supporting means.

20. A keratoprosthesis according to claim 18 wherein said anterior chamber supporting means comprises first substantially parallel strip portions and second substantially parallel strip portions fixedly intersecting said first substantially parallel strip portions, and said anterior chamber supporting means is of a thickness less than the external thread-to-thread gap of said cylindrical lens structure, and wherein said attaching means of said anterior chamber supporting means comprises at least two of said parallel strip portions.

21. A keratoprosthesis according to claim 19 wherein said anterior chamber supporting means is substantially triangularly shaped.

22. A keratoprosthesis according to claim 1 or claim 8 wherein said lens structure comprises an anteriorly removable externally threaded lens portion, a cylindrical internally threaded receptacle for receiving said lens portion, and an posterior end of predetermined curvature for acting as an intraocular permanent lens.

23. A keratoprosthesis according to claim 1 further comprising an intracorneal supporting means conforming substantially to the shape of the cornea and having apertures formed therein.

24. A keratoprosthesis according to claim 1 further comprising an intracorneal supporting means having a portion thereof constructed of a knitted fibrous material.

25. A keratoprosthesis according to claim 22 wherein said intracorneal supporting means is substantially circular in shape.

26. A keratoprosthesis according to claim 1 or claim 8 wherein said lens structure has a threaded outer surface over at least a portion of its length and wherein said anterior chamber supporting means is substantially flat and has a threaded aperture formed therein for attachingly receiving the threads on the outer surface of said lens structure.

27. A keratoprosthesis according to claim 23 wherein said intracorneal supporting means is substantially circular in shape.

28. A keratoprosthesis comprising: (a) a generally cylindrical lens structure, of sufficient length to extend anteriorly into the corneal stroma and posteriorly through the pupil into the posterior chamber, having an externally threaded, cylindrical, removable lens portion, a cylindrical. internally threaded receptacle for receiving said externally threaded removable lens portion, a posterior end of predetermined curvature for functioning as an intraocular permanent lens, and an outer surface which is threaded over at least a portion of its length; (b) an essentially flat anterior chamber means of such planar dimensions and of such shape as to effect the torsional anchoring of said anterior chamber supporting means by contact of its outer edges with the anterior chamber angle and having a threaded aperture formed therein for attachingly receiving said outer surface threads of said lens structure; and, (c) a substantially circular intracorneal supporting means which conforms substantially to the shape of the cornea and which has a central threaded aperture formed therein for attachingly receiving said outer surface threads of said lens structure.

* * * * *